United States Patent [19]
Aman et al.

[11] Patent Number: 5,858,953
[45] Date of Patent: *Jan. 12, 1999

[54] STABILIZED 1-BROMOPROPANE COMPOSITION

[75] Inventors: Shunji Aman; Yoshikazu Oda, both of Yamaguchi, Japan

[73] Assignee: Tosoh Corporation, Yamaguchi, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 627,978

[22] Filed: Apr. 4, 1996

[30] Foreign Application Priority Data

Apr. 12, 1995 [JP] Japan .................................. 7-086888

[51] Int. Cl.⁶ .............................. C11D 7/30; C11D 7/50; C23G 5/028; B08B 3/08
[52] U.S. Cl. ........................ 510/412; 134/40; 252/364; 510/255; 510/256; 510/258; 510/273; 510/365; 570/111; 570/116
[58] Field of Search ................... 510/412, 255, 510/256, 258, 273, 365; 252/364; 134/40; 570/111, 116

[56] References Cited

U.S. PATENT DOCUMENTS

| | | | |
|---|---|---|---|
| 3,730,904 | 5/1973 | Clementson et al. | 252/171 |
| 5,403,507 | 4/1995 | Henry | 252/170 |
| 5,492,645 | 2/1996 | Oshima et al. | 252/171 |
| 5,616,549 | 4/1997 | Clark | 510/412 |
| 5,690,862 | 11/1997 | Moore, Jr. et al. | 252/364 |

FOREIGN PATENT DOCUMENTS

| | | | |
|---|---|---|---|
| 4420082 | 8/1969 | Japan . | |
| 56-166127 | 12/1981 | Japan . | |
| 6-220494 | 8/1994 | Japan | C11D 7/50 |
| 8-67643 | 3/1996 | Japan . | |
| 8-311675 | 11/1996 | Japan . | |
| 2024242 | 1/1980 | United Kingdom . | |

*Primary Examiner*—Christine Skane
*Attorney, Agent, or Firm*—Sughrue, Mion, Zinn, Macpeak & Seas, PLLC

[57] ABSTRACT

A 1-bromopropane composition is disclosed, which stays stable even under the condition that it is repeatedly used at high temperatures over an extended period of time as in vapor degreasing. The stabilized 1-bromopropane composition comprises 100 parts by weight of 1-bromopropane, from 0.1 to 5 parts by weight of nitromethane, and from 0.1 to 5 parts by weight of 1,2-butylene oxide or trimethoxymethane.

12 Claims, No Drawings

STABILIZED 1-BROMOPROPANE COMPOSITION

FIELD OF THE INVENTION

The present invention relates to a stabilized 1-bromopropane composition.

BACKGROUND OF THE INVENTION

For the degreasing of worked parts and precision parts having a large amount of mineral oils and fats attached thereto, metallic parts which are liable to stain or rust, small parts which are handled in a large amount in a cleaning basket, etc., chlorine solvents have been heretofore used for the most part, particularly 1,1,1-trichloroethane, which is a non-aqueous chlorine solvent excellent in properties such as high degreasing power and incombustibility.

In recent years, however, social awareness of global environmental issues has been increasing more and more, and this has led to a growing trend toward severer control on the discharge of environment-destroying substances. For example, 1,1,1-trichloroethane, which has been used in great quantities as an excellent degreasing detergent, is now on the list of substances destroying the ozone layer in the stratosphere. It was decided that the production of 1,1,1-trichloroethane shall be abolished by the end of 1995. Further, other chlorine solvents such as trichloroethylene and perchloroethylene involve environmental problems such as toxicity and contamination of underground water and have thus been gradually placed under restrictions. Accordingly, less pollutive substitute detergents for these chlorine solvents have been keenly demanded.

It is well known that a certain kind of bromohydrocarbon has a high dissolving power for various oils. For example, tribromomethane and 1,2-dibromopropane are described in JP-B-44-20082 (the term "JP-B" as used herein means an "examined Japanese patent publication"). 2,3-Dibromobutane and n-butyl bromide are described in U.S. Pat. No. 3,730,904. 1-Bromopropane and 2-bromopropane are described in JP-A-6-220494.

Among these bromohydrocarbons, 1-bromopropane is incombustible and has a detergent action equal to or higher than that of 1,1,1-trichloroethane but is disadvantageous in that it is liable to cause decomposition reaction induced by various metals such as aluminum, zinc, iron and copper.

The decomposition reaction of 1-bromopropane upon contact with a metal proceeds differently by the kind of the metal. This decomposition reaction shows a marked progress upon contact with aluminum. At ordinary temperatures, this decomposition reaction proceeds very slowly. Upon heating, this reaction involves a chain decomposition reaction while producing hydrogen bromide that eventually vigorously corrodes aluminum to convert 1-bromopropane to a dark brown tar substance. Accordingly, the essential requirement for the use of 1-bromopropane in the cleaning of various metallic parts is the stabilization of 1-bromopropane such that the decomposition of 1-bromopropane induced by various metals, particularly aluminum, is inhibited to prevent the materials to be cleaned and the cleaning apparatus from being corroded.

As an approach for inhibiting the decomposition reaction of 1-bromopropane induced by aluminum there is disclosed in JP-A-6-220494 a method which comprises the use of nitroalkanes, ethers, epoxides or amines singly or in combination as a stabilizer. However, the stabilizer composition disclosed as an example in the above cited Japanese patent application is disadvantageous in that it is not necessarily stable to metals commonly used as industrial metallic materials such as zinc, iron and copper and thus can corrode the materials to be cleaned or cleaning apparatus when used at high temperatures over an extended period of time, such as in vapor degreasing.

SUMMARY OF THE INVENTION

It is therefore an object of the present invention to provide a stabilized 1-bromopropane composition which can be used in the cleaning of various industrial materials, including metallic products of zinc, iron, copper, etc., as well as aluminum, without corroding the articles to be cleaned or cleaning apparatus even after a prolonged use at high temperatures.

The foregoing object of the present invention will become more apparent from the following detailed description and examples.

Under these circumstances, the inventors made extensive studies of the foregoing difficulties. As a result, the desired stabilized 1-bromopropane was found. The present invention has been thus worked out.

The present invention provides a stabilized 1-bromopropane composition, comprising 100 parts by weight of 1-bromopropane, from 0.1 to 5 parts by weight of nitromethane and from 0.1 to 5 parts by weight of 1,2-butylene oxide or trimethoxymethane The present invention further provides a stabilizer for 1-bromopropane, which comprises from 0.1 to 5 parts by weight of nitromethane and from 0.1 to 5 parts by weight of 1,2-butylene oxide or trimethoxymethane.

The present invention also provides a method for improving the stability of 1-bromopropane which comprises adding to 1-bromopropane a stabilizer comprising from 0.1 to 5 parts by weight of nitromethane and from 0.1 to 5 parts by weight of 1,2-butylene oxide or trimethoxymethane, based on 100 parts by weight of 1-bromopropane.

DETAILED DESCRIPTION OF THE INVENTION

The present invention will be further described hereinafter.

A stabilizer to be used in the present invention is a binary composition composed of nitromethane and 1,2-butylene oxide or trimethoxymethane. If this stabilizer lacks even one of the two components, satisfiable effects cannot be exerted.

For example, even if nitromethane is used singly, the decomposition reaction of 1-bromopropane upon contact with a metal can be inhibited. However, under the condition that 1-bromopropane should be repeatedly used at high temperatures over an extended period of time as in vapor degreasing, the water content in 1-bromopropane and 1-bromopropane react with each other to produce hydrogen bromide gas that corrodes the metal. If 1,2-butylene oxide or trimethoxymethane is used singly, no stabilizing effect can be recognized. It is thought that nitromethane inhibits the decomposition reaction of 1-bromopropane upon contact with a metal while 1,2-butylene oxide or trimethoxymethane captures hydrogen bromide gas to attain stabilization. Accordingly, only the combined use of 1-bromopropane and the binary stabilizer according to the present invention can exert a stabilization effect with respect to various metals such as zinc, iron and copper, as well as aluminum. The resulting effective stability can be maintained particularly under the condition that 1-bromopropane should be repeatedly used over an extended period of time at high temperatures as in vapor degreasing. The effective stability can be maintained in cleaning at ordinary temperatures.

The amount of the stabilizer to be added is composed of 0.1 to 5 parts by weight for nitromethane and 0.1 to 5 parts by weight for 1,2-butylene oxide or trimethoxymethane, based on 100 parts by weight of 1-bromopropane. If at least nitromethane and 1,2-butylene oxide or trimethoxymethane are added in an amount of from 0.1 to 1 part by weight and from 0.1 to 1 part by weight, respectively, based on 100 parts by weight of 1-bromopropane, a sufficient stabilization effect can be exerted. If the added amount of these components fall below the above defined lower limit, the desired effect cannot be maintained. On the contrary, even if the added amount of these components exceed the above defined upper limit, no further effects can be expected, though having no problems with the effect itself. This is economically disadvantageous.

The stabilizer according to the present invention may be used in combination with other various stabilizers. Examples of these stabilizers include cyclic ethers such as 1,4-dioxane, 1,3-dioxolane and 1,3,5-trioxane; chain ethers such as 1,2-dimethoxyethane; saturated alcohols such as isopropanol, tert-butyl alcohol and tert-amyl alcohol; unsaturated alcohols such as 2-methyl-3-butyne-2-ol; phenols such as phenol, thymol, 2,6-di-tert-butyl-p-cresol and catechol; and thiocyanic esters such as methyl thiocyanate and ethyl thiocyanate.

The 1-bromopropane composition obtained according to the present invention is useful as a detergent since it can maintain an effective stability without corroding the articles to be cleaned or cleaning apparatus or staining the articles to be cleaned particularly even under the condition that it should be repeatedly used at high temperatures over an extended period of time as in vapor degreasing.

The present invention will be further described in the following examples, but the present invention should not be construed as being limited thereto.

EXAMPLE 1

Into a 50-ml glass test tube was charged 10 ml of a 1-bromopropane composition obtained by adding 0.5 parts by weight of nitromethane and 0.5 parts by weight of 1,2-butylene oxide to 100 parts by weight of 1-bromopropane. An aluminum specimen (specification: JIS A-1100P (the term "JIS" as used herein means "Japanese Industrial Standard"); dimension: 13 mm×65 mm×3 mm) which had been thoroughly polished and cleaned was then placed in the test tube so as to extend over both the gaseous and liquid phases. An air condenser was attached to the top of the test tube and the 1-bromopropane composition was then refluxed in an oil bath. A pH-indicator paper was put in the air condenser. After 96 hours of refluxing, the reaction system was allowed to cool to room temperature. The aluminum specimen was taken out from the tube, and then observed for corrosion. The liquid phase was observed for coloration. Further, the pH-indicator paper was checked to see if hydrogen bromide gas was produced. The content of stabilizer components based on 100 parts by weight of 1-bromopropane and the test results are set forth in Table 1.

TABLE 1

| Test No. | Stabilizer composition (parts by weight)[1] | | | Test Results | | Production of Acidic Gas |
| --- | --- | --- | --- | --- | --- | --- |
| | Nitromethane | 1,2-butylene oxide | Trimethoxy methane | Metal Specimen | Test solution | |
| Example 1 | 0.5 | 0.5 | — | A | A | None |
| Example 2 | 0.5 | 0.1 | — | A | A | None |
| Example 3 | 0.25 | 0.5 | — | A | A | None |
| Example 4 | 0.5 | 1 | — | A | A | None |
| Example 5 | 0.5 | 5 | — | A | A | None |
| Example 6 | 1 | 0.5 | — | A | A | None |
| Example 7 | 3 | 0.5 | — | A | A | None |
| Example 8 | 3 | 3 | — | A | A | None |
| Example 9 | 5 | 0.5 | — | A | A | None |
| Example 10 | 0.25 | — | 0.5 | A | A | None |
| Example 11 | 0.5 | — | 0.1 | A | A | None |
| Example 12 | 0.5 | — | 0.5 | A | A | None |
| Example 13 | 0.5 | — | 1 | A | A | None |
| Example 14 | 0.5 | — | 5 | A | A | None |
| Example 15 | 1 | — | 0.5 | A | A | None |
| Example 16 | 3 | — | 0.5 | A | A | None |
| Example 17 | 3 | — | 3 | A | A | None |
| Example 18 | 5 | — | 0.5 | A | A | None |
| Comparative Example 1 | — | — | — | D | D | Observed |
| Comparative Example 2 | 0.5 | — | — | B | A | Observed |
| Comparative Example 3 | 1 | — | — | B | A | Observed |
| Comparative Example 4 | 3 | — | — | B | A | Observed |
| Comparative Example 5 | — | 3 | — | D | D | Observed |
| Comparative Example 6 | — | 0.5 | — | D | D | Observed |
| Comparative Example 7 | — | — | 1 | D | D | Observed |
| Comparative Example 8 | 0.05 | 0.5 | — | D | D | Observed |

TABLE 1-continued

| Test No. | Stabilizer composition (parts by weight)[1] | | | Test Results | | Production of Acidic Gas |
|---|---|---|---|---|---|---|
| | Nitromethane | 1,2-butylene oxide | Trimethoxy methane | Metal Specimen | Test solution | |
| Comparative Example 9 | 0.05 | — | 0.5 | D | D | Observed |

[1]Addition amount (parts by weight) based on 100 parts by weight of 1-bromopropane The criterion for evaluation of the external appearance of aluminum specimen and coloration of the test solution are as follows:

Criterion for evaluation of metal specimen
  A: No change observed
  B: Tarnish observed slightly on some area
  C: Tarnish observed on the entire area
  D: Definite discoloration or corrosion observed on the entire area Criterion for evaluation of test solution
  A: Colorless and transparent
  B: Slightly colored
  C: Definite coloration observed
  D: Marked coloration observed

EXAMPLES 2–18 AND COMPARATIVE EXAMPLES 1–9

The procedure of Example 1 was followed to examine a 1-bromopropane composition except that the composition and addition amount of the stabilizer according to the present invention were changed. The content of the stabilizer based on 100 parts by weight of 1-bromopropane and the test results are set forth in Table 1.

COMPARATIVE EXAMPLES 10–27

The procedure of Example 1 was followed to examine a 1-bromopropane composition except that the stabilizer was changed. The content of the stabilizer based on 100 parts by weight of 1-bromopropane and the test results are set forth in Table 2.

TABLE 2

| Test No. | Stabilizer | | Conditions After Test | | Production of Acidic Gas |
|---|---|---|---|---|---|
| | Compound Name | Addition Amount[1] | Metal Specimen | Test Solution | |
| Comparative Example 10 | 1,4-Dioxane | 3 | D | D | Observed |
| Comparative Example 11 | 1,2-Dimethoxyethane | 5 | D | D | Observed |
| Comparative Example 12 | Acetone | 3 | D | D | Observed |
| Comparative Example 13 | 1,3-Dioxolane | 3 | A | A | Observe& |
| Comparative Example 14 | Methyl ethyl ketone | 3 | D | D | Observed |
| Comparative Example 15 | sec-Butyl alcohol | 3 | D | D | Observed |
| Comparative Example 16 | tert-Butyl alcohol | 3 | D | D | Observed |
| Comparative Example 17 | 2-Methyl-3-butyne-2-ol | 3 | D | D | Observed |
| Comparative Example 18 | n-Propanol | 3 | D | D | Observed |
| Comparative Example 19 | Isopropanol | 3 | D | D | Observed |
| Comparative Example 20 | Diisopropylamine | 3 | D | D | Observed |
| Comparative Example 21 | Triethylamine | 3 | D | D | Observed |
| Comparative Example 22 | Tetrahydrofuran | 3 | D | D | Observed |
| Comparative Example 23 | Tetrahydropyran | 3 | D | D | Observed |
| Comparative Example 24 | Diisopropyl ether | 3 | D | D | Observed |
| Comparative Example 25 | Ethyl acetate | 3 | D | D | Observed |
| Comparative Example 26 | 2-Methoxy ethanol | 3 | D | D | Observed |
| Comparative Example 27 | Methylal | 3 | D | D | Observed |

[1]Addition amount (parts by weight) based on 100 parts by weight of 1-bromopropane

EXAMPLE 19

Into a 100-ml glass Erlenmeyer flask was charged 50 ml of a 1-bromopropane composition obtained by adding 0.5 parts by weight of nitromethane and 0.5 parts by weight of 1,2-butylene oxide to 100 parts by weight of 1-bromopropane. A piece of a metal specimen (dimension: 13 mm×65 mm×3 mm) which had been thoroughly polished and cleaned was then placed in the Erlenmeyer flask so as to extend over both the gaseous and liquid phases. With a reflux condenser attached to the top thereof, the Erlenmeyer flask was then heated over a hot water bath to the boiling temperature of the 1-bromopropane composition where it was refluxed with the specimen being in contact with both the gaseous and liquid phases. After 140 hours of refluxing, the reaction system was allowed to cool to room temperature. The specimen was then taken out from the flask to see the corrosion thereof. The liquid phase was observed for coloration. The acid content (hydrogen bromide) produced was then titrimetrically determined. The content of the stabilizer based on 100 parts by weight of 1-bromopropane and the test results are set forth in Table 3 and Table 4, respectively.

TABLE 3

| Test No. | Nitromethane | 1,2-Butylene oxide | Trimethoxymethane | Nitroethane | 1,4-Dioxane | 1,2-Dimethoxy ethane | 2-Methoxyethanol | Triethanolamine | N,N-Diisopropylethylamine | Methyl thiocyanate |
|---|---|---|---|---|---|---|---|---|---|---|
| Example 19 | 0.5 | 0.5 | — | — | — | — | — | — | — | — |
| Example 20 | 0.25 | 0.5 | — | — | — | — | — | — | — | — |
| Example 21 | 0.5 | 0.1 | — | — | — | — | — | — | — | — |
| Example 22 | 0.5 | 1 | — | — | — | — | — | — | — | — |
| Example 23 | 0.5 | 5 | — | — | — | — | — | — | — | — |
| Example 24 | 1 | 0.5 | — | — | — | — | — | — | — | — |
| Example 25 | 3 | 0.5 | — | — | — | — | — | — | — | — |
| Example 26 | 3 | 3 | — | — | — | — | — | — | — | — |
| Example 27 | 5 | 0.5 | — | — | — | — | — | — | — | — |
| Example 28 | 0.25 | — | 0.5 | — | — | — | — | — | — | — |
| Example 29 | 0.5 | — | 0.1 | — | — | — | — | — | — | — |
| Example 30 | 0.5 | — | 0.5 | — | — | — | — | — | — | — |
| Example 31 | 0.5 | — | 1 | — | — | — | — | — | — | — |
| Example 32 | 0.5 | — | 5 | — | — | — | — | — | — | — |
| Example 33 | 1 | — | 0.5 | — | — | — | — | — | — | — |
| Example 34 | 3 | — | 0.5 | — | — | — | — | — | — | — |
| Example 35 | 3 | — | 3 | — | — | — | — | — | — | — |
| Example 36 | 5 | — | 0.5 | — | — | — | — | — | — | — |
| Example 37 | 0.2 | 0.5 | — | — | — | — | — | — | — | 0.01 |
| Example 38 | 0.2 | 0.5 | — | — | — | — | — | — | — | 0.1 |
| Comparative Example 28 | — | — | — | — | — | — | — | — | — | — |
| Comparative Example 29 | 0.5 | — | — | — | — | — | — | — | — | — |
| Comparative Example 30 | — | 0.5 | — | — | — | — | — | — | — | — |
| Comparative Example 31 | — | — | 0.5 | — | — | — | — | — | — | — |
| Comparative Example 32 | 0.05 | 0.5 | — | — | — | — | — | — | — | — |
| Comparative Example 33 | — | 0.5 | — | — | — | 0.5 | — | — | — | — |
| Comparative Example 34 | — | 0.5 | — | — | 0.5 | — | — | — | — | — |
| Comparative Example 35 | 2 | — | — | — | — | — | — | — | — | — |
| Comparative Example 36 | 2 | — | — | — | — | — | — | 1 | — | — |
| Comparative Example 37 | 2 | — | — | — | — | — | — | — | 1 | — |
| Comparative Example 38 | — | 0.5 | — | 0.5 | — | — | — | — | — | — |
| Comparative Example 39 | — | 0.5 | — | 1 | — | — | — | — | — | — |
| Comparative Example 40 | — | 0.5 | — | 3 | — | — | — | — | — | — |
| Comparative Example 41 | 0.2 | 0.5 | — | — | 3 | — | — | — | — | — |
| Comparative Example 42 | — | — | — | 2 | — | — | 0.5 | — | — | — |
| Comparative Example 43 | — | — | — | 2 | — | — | — | — | 0.5 | — |
| Comparative Example 44 | — | — | — | 2 | — | — | 0.5 | — | 0.1 | — |

[1] Addition amount (parts by weight) based on 100 parts by weight of 1-bromopropane

TABLE 4

| Test No. | Aluminum | | | Zinc | | | Iron | | | Copper | | |
|---|---|---|---|---|---|---|---|---|---|---|---|---|
| | After Test | | HBr | After Test | | HBr | After Test | | HBr | After Test | | HBr |
| | Metal Specimen | Test Solution | Concentration (ppm) | Metal Specimen | Test Solution | Concentration (ppm) | Metal Specimen | Test Solution | Concentration (ppm) | Metal Specimen | Test Solution | Concentration |
| Example 19 | A | A | 0 | A | A | 0 | A | A | 0 | A | A | 0 |
| Example 20 | A | A | 0 | A | A | 0 | A | A | 0 | A | A | 0 |
| Example 21 | A | A | 0 | A | A | 0 | A | A | 0 | A | A | 0 |
| Example 22 | A | A | 0 | A | A | 0 | A | A | 0 | A | A | 0 |
| Example 23 | A | A | 0 | A | A | 0 | A | A | 0 | A | A | 0 |
| Example 24 | A | A | 0 | A | A | 0 | A | A | 0 | A | A | 0 |
| Example 25 | A | A | 0 | A | A | 0 | A | A | 0 | A | A | 0 |
| Example 26 | A | A | 0 | A | A | 0 | A | A | 0 | A | A | 0 |
| Example 27 | A | A | 0 | A | A | 0 | A | A | 0 | A | A | 0 |
| Example 28 | A | A | 0 | A | A | 0 | A | A | 0 | A | A | 0 |
| Example 29 | A | A | 0 | A | A | 0 | A | A | 0 | A | A | 0 |
| Example 30 | A | A | 0 | A | A | 0 | A | A | 0 | A | A | 0 |
| Example 31 | A | A | 0 | A | A | 0 | A | A | 0 | A | A | 0 |
| Example 32 | A | A | 0 | A | A | 0 | A | A | 0 | A | A | 0 |
| Example 33 | A | A | 0 | A | A | 0 | A | A | 0 | A | A | 0 |
| Example 34 | A | A | 0 | A | A | 0 | A | A | 0 | A | A | 0 |
| Example 35 | A | A | 0 | A | A | 0 | A | A | 0 | A | A | 0 |
| Example 36 | A | A | 0 | A | A | 0 | A | A | 0 | A | A | 0 |
| Example 37 | A | A | 0 | A | A | 0 | A | A | 0 | A | A | 0 |
| Example 38 | A | A | 0 | A | A | 0 | A | A | 0 | A | A | 0 |
| Comparative Example 28 | D | D | Note[1] | D | D | Note[1] | C | B | 0 | C | B | 0 |
| Comparative Example 29 | B | A | 10 | B | A | 10 | B | A | 10 | C | B | 10 |
| Comparative Example 30 | D | D | Note[1] | D | B | 34 | B | A | 0 | C | B | 24 |
| Comparative Example 31 | D | D | Note[1] | B | A | 0 | B | A | 0 | B | A | 0 |
| Comparative Example 32 | D | D | Note[1] | D | B | 10 | B | B | 0 | B | B | 0 |
| Comparative Example 33 | D | D | Note[1] | D | B | 10 | B | B | 0 | B | B | 0 |
| Comparative Example 34 | D | D | Note[1] | D | D | Note[1] | C | B | 10 | C | B | 0 |
| Comparative Example 35 | A | A | 10 | D | B | 34 | D | D | Note[1] | C | B | 20 |
| Comparative Example 36 | C | D | Note[2] | C | D | Note[2] | C | D | Note[2] | C | D | Note[2] |
| Comparative Example 37 | C | D | Note[2] | C | D | Note[2] | C | D | Note[2] | C | D | Note[2] |
| Comparative Example 38 | D | D | Note[1] | B | B | 22 | B | B | 48 | B | B | 22 |
| Comparative Example 39 | B | B | 34 | B | B | 34 | B | B | 35 | B | B | 35 |
| Comparative Example 40 | B | B | 66 | B | B | 100 | B | B | 83 | B | B | >100 |
| Comparative Example 41 | B | B | 30 | D | B | 10 | C | C | 10 | C | C | 10 |
| Comparative Example 42 | C | A | 0 | D | B | 0 | D | D | >100 | D | D | Note[1] |
| Comparative Example 43 | D | A | 0 | D | B | 0 | D | D | 20 | D | D | Note[1] |
| Comparative Example 44 | A | A | 0 | D | B | 0 | D | B | 20 | D | D | Note[1] |

Note [1]: Acid content was immeasurable due to marked deterioration of the test solution.
Note [2]: Test was suspended due to formation of precipitation in the test solution.

The material of the metal specimens used were as follows:
Aluminum specimen: JIS A1100P
Zinc specimen: JIS Second-Grade (for flat board)
Iron specimen: JIS cold-pressed steel plate SPCC
Copper specimen: JIS First-Grade copper plate (ordinary class)
The criterion for evaluation of the external appearance of the metal specimen and the coloration of the test solution are as follows:
Criterion for evaluation of metal specimen
A: No change observed
B: Tarnish observed slightly on some area
C: Tarnish observed on the entire area
D: Definite discoloration or corrosion observed on the entire area
Criterion for evaluation of test solution
A: Colorless and transparent
B: Slightly colored
C: Definite coloration observed
D: Marked coloration observed

EXAMPLES 20–38 AND COMPARATIVE EXAMPLES 28–44

The procedure of Example 19 was followed to examine a 1-bromopropane composition except that the composition and addition amount of the stabilizer according to the present invention were changed. The content of the stabilizer based on 100 parts by weight of 1-bromopropane is set forth in Table 3 and the test results are set forth in Table 4.

Tables 3 and 4 show that the 1-bromopropane compositions of the present invention exhibit a sufficient stability against aluminum, zinc, iron and copper. On the contrary, the stabilizer combinations of the Comparative Examples, though exerting a stabilization effect with respect to a certain kind of metal, exert an insufficient stabilization effect with respect to other metals.

While the invention has been described in detail and with reference to specific embodiments thereof, it will be apparent to one skilled in the art that various changes and modifications can be made therein without departing from the spirit and scope thereof.

What is claimed is:

1. A stabilized 1-bromopropane composition, consisting of 100 parts by weight of 1-bromopropane, from 0.1 to 5 parts by weight of nitromethane, and from 0.1 to 5 parts by weight of 1,2-butylene oxide or trimethoxymethane, and optionally a stabilizer selected from the group consisting of saturated alcohols, unsaturated alcohols, phenols and thiocyanic esters.

2. The stabilized 1-bromopropane composition of claim 1, which consists of 100 parts by weight of 1-bromopropane, from 0.1 to 1 part by weight of nitromethane and from 0.1 to 1 part by weight of 1,2-butylene oxide or trimethoxymethane, and optionally a stabilizer selected from the group consisting of saturated alcohols, unsaturated alcohols, phenols and thiocyanic esters.

3. The stabilized 1-bromopropane composition of claim 1, which consists of 100 parts by weight of 1-bromopropane, from 0.1 to 1 part by weight of nitromethane and from 0.1 to 1 part by weight of 1,2-butylene oxide, and optionally a stabilizer selected from the group consisting of saturated alcohols, unsaturated alcohols, phenols and thiocyanic esters.

4. The stabilized 1-bromopropane composition of claim 1, consisting of 100 parts by weight of 1-bromopropane, from 0.1 to 5 parts by weight of nitromethane and from 0.1 to 5 parts by weight of 1,2-butylene oxide, and optionally a stabilizer selected from the group consisting of saturated alcohols, unsaturated alcohols, phenols and thiocyanic esters.

5. The stabilized 1-bromopropane composition of claim 1, consisting of 100 parts by weight of 1-bromopropane, from 0.1 to 5 parts by weight of nitromethane, and from 0.1 to 5 parts by weight of trimethoxymethane, and optionally a stabilizer selected from the group consisting of saturated alcohols, unsaturated alcohols, phenols and thiocyanic esters.

6. The stabilized 1-bromopropane composition of claim 1, which consists of 100 parts by weight of 1-bromopropane, from 0.1 to 1 part by weight of nitromethane and from 0.1 to 1 part by weight of trimethoxymethane, and optionally a stabilizer selected from the croup consisting of saturated alcohols, unsaturated alcohols, phenols and thiocyanic esters.

7. A method for improving the stability of 1-bromopropane which consists of adding to 1-bromopropane a stabilizer consisting of from 0.1 to 5 parts by weight of nitromethane and from 0.1 to 5 parts by weight of 1,2-butylene oxide or trimethoxymethane, based on 100 parts by weight of 1-bromopropane, and optionally a stabilizer selected from the group consisting of saturated alcohols, unsaturated alcohols, phenols and thiocyanic esters.

8. The method for improving the stability of 1-bromopropane of claim 7 which consists of adding to 1-bromopropane a stabilizer consisting of from 0.1 to 5 parts by weight of nitromethane and from 0.1 to 5 parts by weight of 1,2-butylene oxide, based on 100 parts by weight of 1-bromopropane, and optionally a stabilizer selected from the group consisting of saturated alcohols, unsaturated alcohols, phenols and thiocyanic esters.

9. The method for improving the stability of 1-bromopropane of claim 7 which consists of adding to 1-bromopropane a stabilizer consisting of from 0.1 to 5 parts by weight of nitromethane and from 0.1 to 5 parts by weight of trimethoxymethane, based on 100 parts by weight of 1-bromopropane, and optionally a stabilizer selected from the group consisting of saturated alcohols, unsaturated alcohols, phenols and thiocyanic esters.

10. The method for improving the stability of 1-bromopropane of claim 7 which consists of adding to 1-bromopropane a stabilizer consisting of from 0.1 to 1 parts by weight of nitromethane and from 0.1 to 1 parts by weight of 1,2-butylene oxide or trimethoxymethane, based on 100 parts by weight of 1-bromopropane, and optionally a stabilizer selected from the group consisting of saturated alcohols, unsaturated alcohols, phenols and thiocygnic esters.

11. The method for improving the stability of 1-bromopropane of claim 7 which consists of adding to 1-bromopropane a stabilizer consisting of from 0.1 to 1 parts by weight of nitromethane and from 0.1 to 1 parts by weight of 1,2-butylene oxide, based on 100 parts by weight of 1-bromopropane, and optionally a stabilizer selected from the group consisting of saturated alcohols, unsaturated alcohols, phenols and thiocyanic esters.

12. The method for improving the stability of 1-bromopropane of claim 7 which consists of adding to 1-bromopropane a stabilizer consisting of from 0.1 to 1 parts by weight of nitromethane and from 0.1 to 1 parts by weight of trimethoxymethane, based on 100 parts by weight of 1-bromopropane, and optionally a stabilizer selected from the group consisting of saturated alcohols, unsaturated alcohols, phenols and thiocyanic esters.

* * * * *